(12) United States Patent
Sutter

(10) Patent No.: US 6,247,932 B1
(45) Date of Patent: Jun. 19, 2001

(54) CONTAINER HOLDING A CARTRIDGE AND A DENTAL IMPLANT ARRANGED THEREIN

(75) Inventor: Franz Sutter, Bennwilerstrasse 42, CH-4435 Niederdorf (CH)

(73) Assignee: Franz Sutter, Niederdorf (CH)

( * ) Notice: Subject to any disclaimer, the term of this patent is extended or adjusted under 35 U.S.C. 154(b) by 0 days.

(21) Appl. No.: 09/424,510
(22) PCT Filed: May 19, 1998
(86) PCT No.: PCT/EP98/02938
  § 371 Date: Feb. 17, 2000
  § 102(e) Date: Feb. 17, 2000
(87) PCT Pub. No.: WO98/53755
  PCT Pub. Date: Dec. 3, 1998

(30) Foreign Application Priority Data

May 26, 1997 (CH) .................................................. 1233/97

(51) Int. Cl.[7] ..................................................... A61C 5/00
(52) U.S. Cl. ............................................. 433/173; 206/368
(58) Field of Search .................................... 433/172, 173, 433/174, 201.1; 206/83, 368, 369, 438; 215/227, DIG. 3

(56) References Cited

U.S. PATENT DOCUMENTS

| 5,062,800 | * | 11/1991 | Niznick ............................. 433/173 |
| 5,368,160 | * | 11/1994 | Leuschen et al. .................... 433/174 |
| 5,558,230 | * | 9/1996 | Fischer et al. ....................... 433/174 |
| 5,582,299 | * | 12/1996 | Lazzara et al. ...................... 206/431 |
| 5,636,991 | * | 6/1997 | Mays ................................... 206/368 |
| 5,755,575 | * | 5/1998 | Biggs ................................... 433/174 |

* cited by examiner

Primary Examiner—Todd E. Manahan
(74) Attorney, Agent, or Firm—Evenson, McKeown, Edwards & Lenahan, P.L.L.C.

(57) ABSTRACT

The case (1) comprises a receptacle (41) with two detachably interconnected receptacle parts (42, 43). The receptacle (41) contains a dental implant (11) and a holder (61). The dental implant (11) has an anchoring section (15) designed to be anchored in a bone, i.e., an outside thread, and an outer section (16) indented to jut out from the bone. The holder (61) engages the outer section (16) of the dental implant (11) and detachably secures it using clamping and/or locking means (67). The dental implant (11) and the holder (61) are connected to each other by anti-rotation means (31, 72) preventing rotations around a common axis (13). Once the case has been opened (41), the holder (61) can be gripped manually or using a tool or instrument and the dental implant (11) held by the holder (61) can be inserted into a bone in the mouth of a patient by screwing, pushing or pressing said implant into the bone.

20 Claims, 4 Drawing Sheets

CONTAINER HOLDING A CARTRIDGE AND A DENTAL IMPLANT ARRANGED THEREIN

TECHNICAL FIELD

The invention relates to a container or device holding a cartridge having two cartridge parts joined separably together and a dental implant arranged in the cartridge.

STATE OF THE ART

A sterile container for a dental implant appearing in the book, "Orale Implantologie," by André Schroeder, Franz Sutter, Daniel Buser and Gisbert Krekeler, 2nd Edition, 1994, Georg Theme Verlag, Stuttgart/New York, pages 223 to 225, contains a cartridge with an ampule and a cap. In the container there is arranged an inner ampule with an inner cap. The inner ampule contains a metal, cage-like holder which holds the dental implant. The implant has, for example, an external thread designed to be screwed into a bone, and an axial bore with an internal thread. When such an implant is unpacked and used, first the outer ampule is opened, the inner ampule dumped out, the inner ampule is opened and a driving instrument is first screwed by hand loosely into the internal thread. Then a ratchet is pushed onto part of the driving instrument, a wrench is tightened onto a part of the driving instrument that bears a hexagonal head and extends through the ratchet and the holder is removed from the container. Then the direction of rotation of the ratchet drill is reversed, the implant is lifted out of the inner ampule and is screwed into the bone.

This known container has the disadvantages that it has relatively many components, and that, above all, many steps are necessary for removing the implant from the container, introducing it with the ratchet into the patient's mouth and driving it in. Also, the driving instrument must be unscrewed from the implant after the implant has been screwed into a bone. The great number of working steps, and especially the screwing of a driving instrument into the implant further increases the danger that germs may get on the implant.

The known container also has similar disadvantages when the implant is not screwed into a bone but is to be hammered into it.

OUTLINE OF THE INVENTION

The invention is addressed to the problem of creating a container and device which will avoid the disadvantages of the known container and especially will make it possible to remove an implant in a few steps from the container and insert it into a bone in the lower or upper jaw of a patient.

The problem is solved according to the invention by a container holding a cartridge having two cartridge parts detachably joined together and a dental implant arranged therein. The dental implant has an anchoring portion intended for anchoring in a bone, and an outer portion intended to protrude from the bone. The container is characterized in that the cartridge contains a holder which can be removed together with the dental implant from the cartridge and which clutches the outer portion of the dental implant, and has clasping and/or holding means detachably holding the implant plus a shaft [axis?], and in that the dental implant and the holder have antirotational means in order to join the dental implant and the holder together against rotation on one another.

Advantageous embodiments of the subject of the invention will be found in the dependent claims.

BRIEF DESCRIPTION OF THE DRAWINGS

The subject matter of the invention will be explained hereinafter with the aid of embodiments represented in the drawings, wherein.

DESCRIPTION OF THE PREFERRED EMBODIMENT

Figure 1:
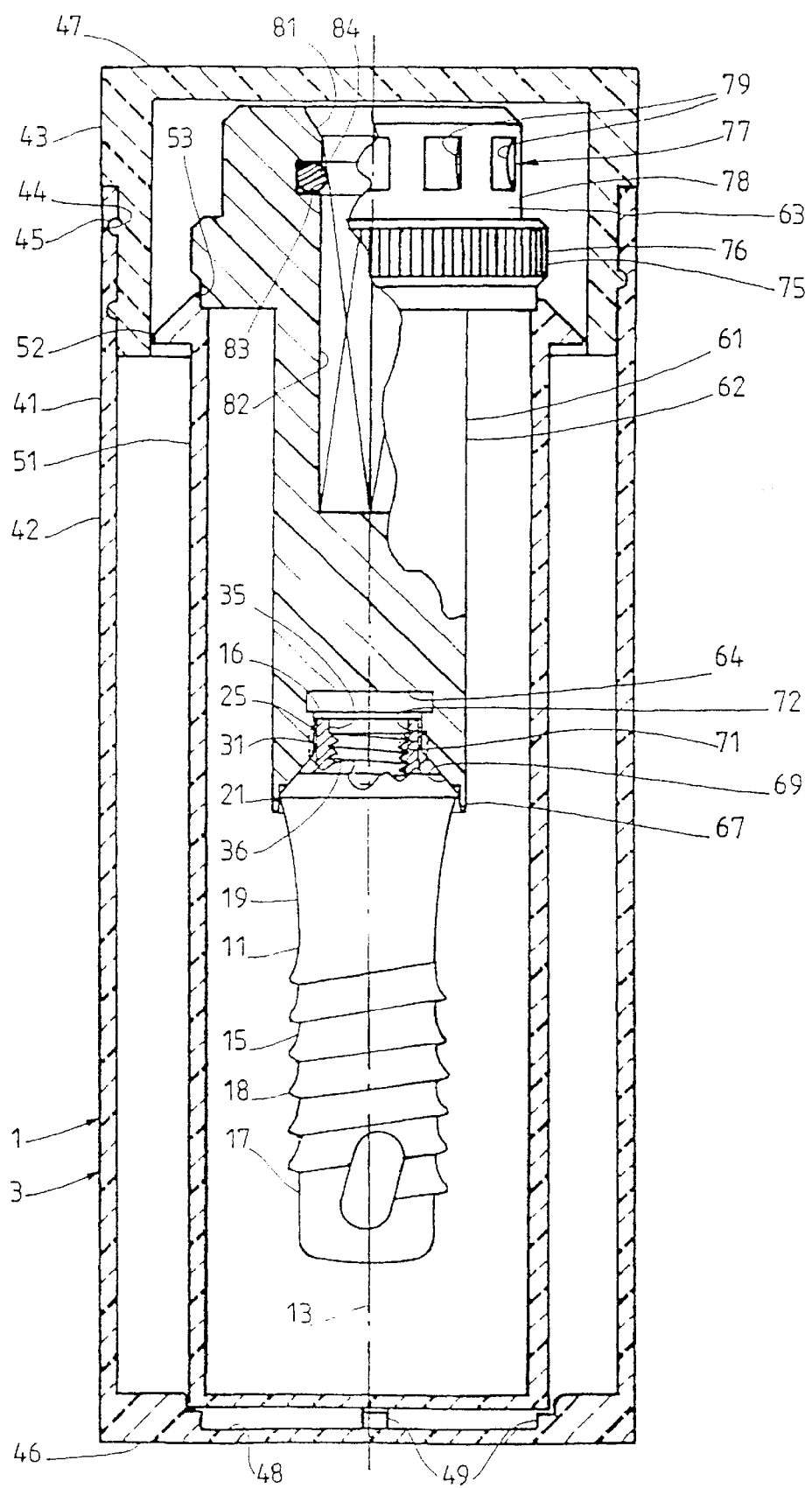
FIG. 1 is an axial section through a container with a dental implant and a holder, FIG. 2 an enlarged detail of FIG. 1, FIG. 3 a cutaway view of an implant and another holder separate from the latter, FIG. 4 an axial section through an implant and, in the left half, through the holder of FIG. 3, and in the right half, through another holder, and FIG. 5 an axial section through an implant and yet another holder.
Figure 2:
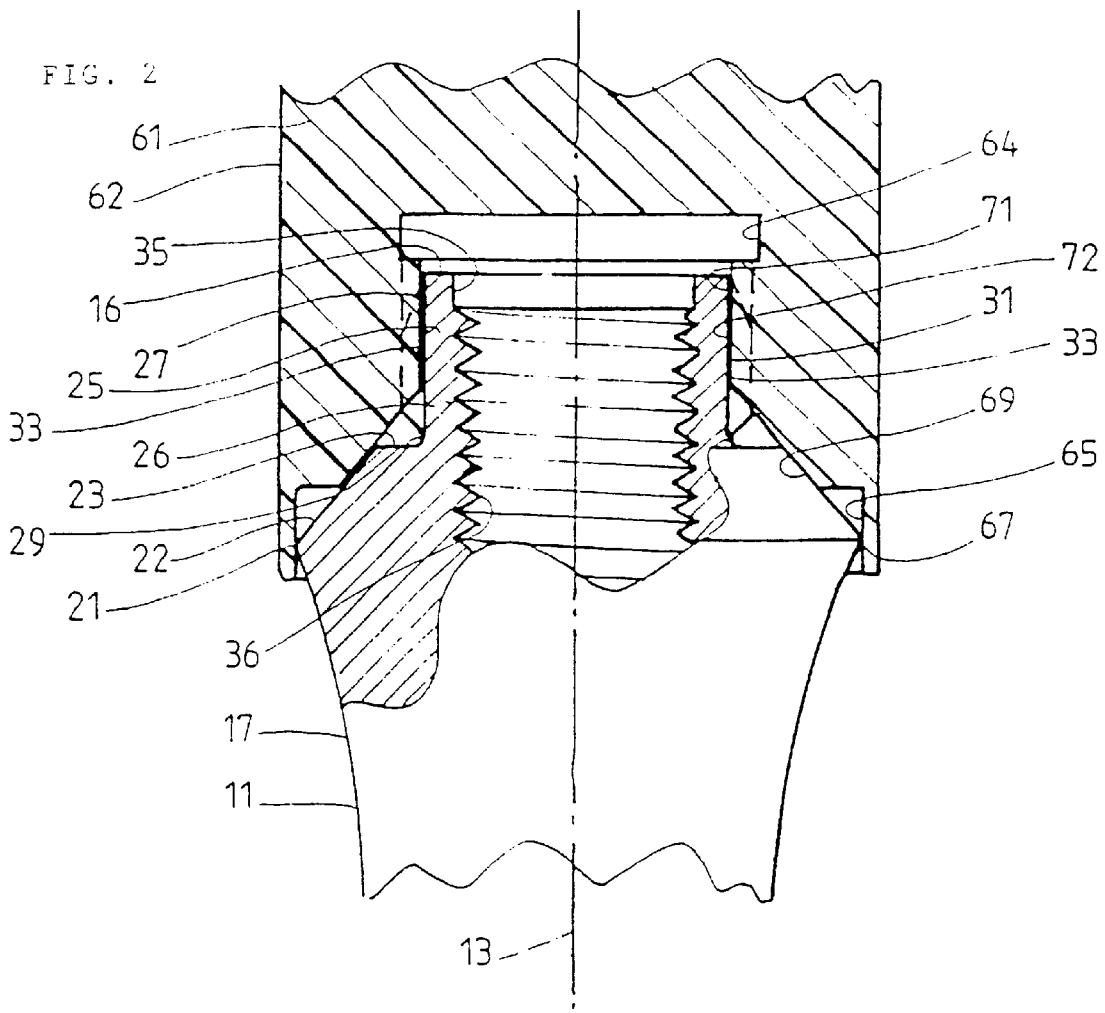

The device 1 seen in FIGS. 1 and 2 has a container 3 with a dental implant 11. The implant and the entire container 3 are generally rotationally symmetrical with an axis 13. The dental implant 11 has an anchoring portion 15 provided for anchoring in a bone of the lower or upper jaw of a patient, and an outer portion (16) which is to protrude from the bone. The implant 11 has a generally cylindrical section 17, which is provided with an external thread 18 which is self-tapping, for example, but could consist of a non-self-tapping, mating thread. The cylindrical section 17 is adjoined by an upwardly flaring, trumpet-shaped section 19 whose bottom portion together with the cylindrical section 17 forms the anchoring portion 15.

At the upper, wider end of the trumpet-shaped section 19 there is a shoulder 21 with a conical shoulder surface 22 that is inclined upwardly and inwardly, forming with the axis 13 an angle of 40° to 50°, for example, 45°. The upper, narrower end of the conical shoulder surface 22 is adjoined at right angles by a planar annular surface 23.

A head 25 extends upward from the annular surface 23 and, together with the upper end of the trumpet-shaped section 19 and shoulder 21, forms the outer portion 16 of the implant 11. The head 25 has a top section 26 and tapering away from the latter toward the free end of the head and thus toward the upper end of the entire implant. The head section 26 parallel to the axis is separated from the upper end of the shoulder 21 by an annular groove 29 which is concavely curved in axial section. The head has a planar, annular end face at its free end. The two head sections 26 and 27 are generally rotationally symmetrical with the axis 13 and/or have each at least an envelope surface rotationally symmetrical with the axis, namely a cylindrical and a conical envelope surface, respectively. The two head sections 26 and 27, however, are provided with anti-rotational and positioning means 31. These are anti-rotational and positioning grooves 33 distributed around the axis 13 and parallel thereto. They are, for example, arcuate, U-shaped, quadrangular or V-shaped in cross section and thus have positioning surfaces which are anti-rotational with respect to the axis 13. The grooves 33 can be all equal in shape, of the same dimensions, and uniformly distributed about the axis. However, several equal grooves as well as one wider and/or deeper groove may be present.

The implant furthermore has a bore 35 coaxial with the axis 13, which opens into the free end of the head 25 and has a section with an internal thread 36 starting approximately at the mouth of the bore.

The container 3 has an elongated cartridge 41. The latter consists of a first, larger cartridge part 42, namely a body also identified by 42, and a second, smaller cartridge part 43, which will also be referred to hereinafter as the cover 43. The two cartridge parts, 42 and 43, consist of a thermoplastic, at least the first cartridge part 42 being transparent.

The two cartridge parts 42 and 43 have a substantially cylindrical shape. They have sections that mate with one another and are provided with an internal thread 44 and an external thread 45, respectively and can be screwed together, i.e., they are joined together separably. The interfitting sections of the two cartridge parts and their threads are configured such that the interior of the cartridge is at least approximately tightly sealed and so isolated from the environment that no germs, microorganisms and viruses can pass from the environment into the interior of the cartridge. The two cartridge parts 43 and 42 have a bottom 46 and a top wall 47. The bottom is provided with a circular recess 48 and a number of cogs 49 disposed at the margin of its bottom.

The container 41 contains an interior cartridge 51 which can be removed from the container. It consists of a body with a cylindrical exterior, which is closed at the bottom end with a floor and is open at the upper end. The interior cartridge consists of a thermoplastic and is transparent. The bottom end of the interior cartridge 51 extends with some clearance into the recess 48 and lies on the cogs 49. The upper end of the inner cartridge 51 extends slightly into the cover 43 where it is provided with an annular, outwardly reaching projection 52 which radially supports and centers the inner cartridge in the interior surface of the cover.

The interior of the inner cartridge 51 is mostly cylindrical, but at the open upper end it has a short and small lip 53.

The container 41 contains a holder 61 which holds the dental implant 11 releasably, can be removed from the container together with the latter, and can serve as a screwing and/or hammering and/or pressing instrument for the implant. The holder 61 is, like the implant, the container 41 and the inner cartridge, generally rotationally symmetrical with the axis 13. The holder 61 has a shaft 62 and, at the upper end, a head projecting radially beyond the shaft. The lower end of the head rests in the lip 53 of the inner cartridge. The lip 53 preferably provides a light press-fit for the head and holds it lightly. The head 63 therefore closes the upper, open end of the inner cartridge 51. The upper end of the head 63 is approximately at the inside surface of the top 47 of the cover 43, so that when the container 41 is closed the head will be unable to move past the lip 53. The shaft 62 is provided at its bottom end remote from the head 63 with a generally rotationally symmetrical, stepped blind bore 64 coaxial with the axis 13. The bore 64 has at the bottom end of the holder a short, cylindrical section 65. The latter is defined in cross section by a thin and short, substantially hollow cylindrical, elastically deformable, especially radially stretchable shaft end section which forms catch and/or clamping means 67. These surround the annular edge in cross section formed by the upper end of the trumpet-shaped section 19 and the outer margin of the conical shoulder surface 22 of the implant, project downward in the axial direction beyond the edge, are under a bias produced by radial elastic force and releasably clutch the implant 11 tightly by this shoulder 21. The cylindrical bore section 65 is adjoined at the top by a bore section tapering upward from the mouth of the bore with a conical contact surface 69. This forms with the axis 13 the same angle as the conical shoulder surface 22 and lies against the latter. The upper end of the conical contact surface 69 follows a bore section 71 parallel to the axis 13. This contains at least a part of the head 25 of the implant, is generally cylindrical and guides and centers the head with slight radial clearance. The bore section 71 has antirotational means 72 which are formed by axially parallel, elongated, rib-like projections which have antirotational surfaces which are not rotationally symmetrical with the axis 13; they engage the antirotational grooves 33 in the head 25 of the implant and join the implant anti-rotationally as regards rotation about the axis 13. Near its bottom end, the head 63 has a rim 75 which projects radially beyond the rest of the head and is provided with ridges or roughening 76 formed, for example, by knurling or cording. The holder 61 is furthermore provided at its end formed by the head 63 with coupling means 77 in order to attach the holder releasably and antirotationally as regards rotation about the axis 13 to a screwing and/or hammering and/or pressing tool. Above the rim 75, the head 63 of the holder 61 has a cylindrical section 79 with milled recesses 78 distributed uniformly along its circumference and serving for the formation of coupling means. The cylindrical section 78 is configured such that an annular coupling means of a ratchet serving as a screwing tool can be placed onto the holder over the cylindrical section 78 and then can contact the rim 75 and engage the recesses 79 with drivers. The coupling means 77 furthermore has a blind bore 81 coaxial with the axis 13, which opens into the free end of the head 63 facing away from the shaft 62, is at least partially polyhedral, square for example, and has a polyhedral bore section 82 that is square, for example, as well as an annular groove 83. The latter holds a rubber-elastic ring 84, an O-ring for example, which projects at least at points out of the annular groove 83 toward the axis 13. A screwdriving tool with a polyhedral key fitting into the bore section 82 can then be inserted into the blind hole 81. The ring 84 then grips the key somewhat tightly, although of course the key can still move axially and can be removed again from the blind hole 81. The shaft 62, the head 63, the gripping and/or clutching means 67, the antirotational means 72 and the entire holder 61 with the exception of the rubber-elastic ring 84, consist of an integral body of thermoplastic material.

The implant 11 is inserted by its manufacturer with an approximately axial thrust into the bore 64 of the holder 61. The holder then clutches the implant by its outer portion 16 and holds it fast. Then the implant and the shaft 62 of the holder a reinserted into the internal cartridge 51, so that the head 63 of the holder 61 enters into the lip 53 of the inner cartridge and closes it. Then the inner cartridge 51 and the holder 61 are inserted into the container 41. After the latter is closed the surfaces of the container adjoining the container's interior, and all parts contained therein, are sterilized.

When a dentist wishes to use the dental implant to bold and/or form a dental prosthesis, he makes a bore in a bone of the lower or upper jaw of a patient to anchor the implant, unscrews the cover 43 from the first container part 42 and dumps the inner cartridge with the holder it contains onto a support. Then the dentist can grasp the head of the holder with two fingers, for example, and tilt the head by applying a light lateral force and release it from the inner cartridge. Then the dentist can withdraw the implant held by the holder 61 without touching the implant, draw it out by the holder from the inner cartridge, insert into the patient's mouth, and drive the implant by manual rotation of the holder into the bore made in the bone. The holder serves in that case as a screwdriving implement. When the implant has been driven partially into the bone, the dentist can also engage the holder with a screwdriving tool, for example a ratchet or a polyhedral wrench fitting the bore 81, or a so-called "floating" screwdriving tool having a socket fitting the blind bore 81 and screw the implant tight by turning the holder.

In an alternative procedure, the dentist, after opening the container 41, can place a ratchet onto the head 63 of the holder 61, or join another screwdriving tool or instrument releasably to the holder and insert the holder as well as the implant it holds, with the ratchet or other tool or instrument, into the patient's mouth and insert it into the bone.

When the implant is tightened and its anchoring portion 15 has been anchored in the bone, the holder attached to the outer portion 16 of the implant can be withdrawn from the holder in an approximately axial direction and taken apart. The implant can thus, with a few, simple steps, be taken from the sterile container 3 and inserted into a bone.

Figure 3:
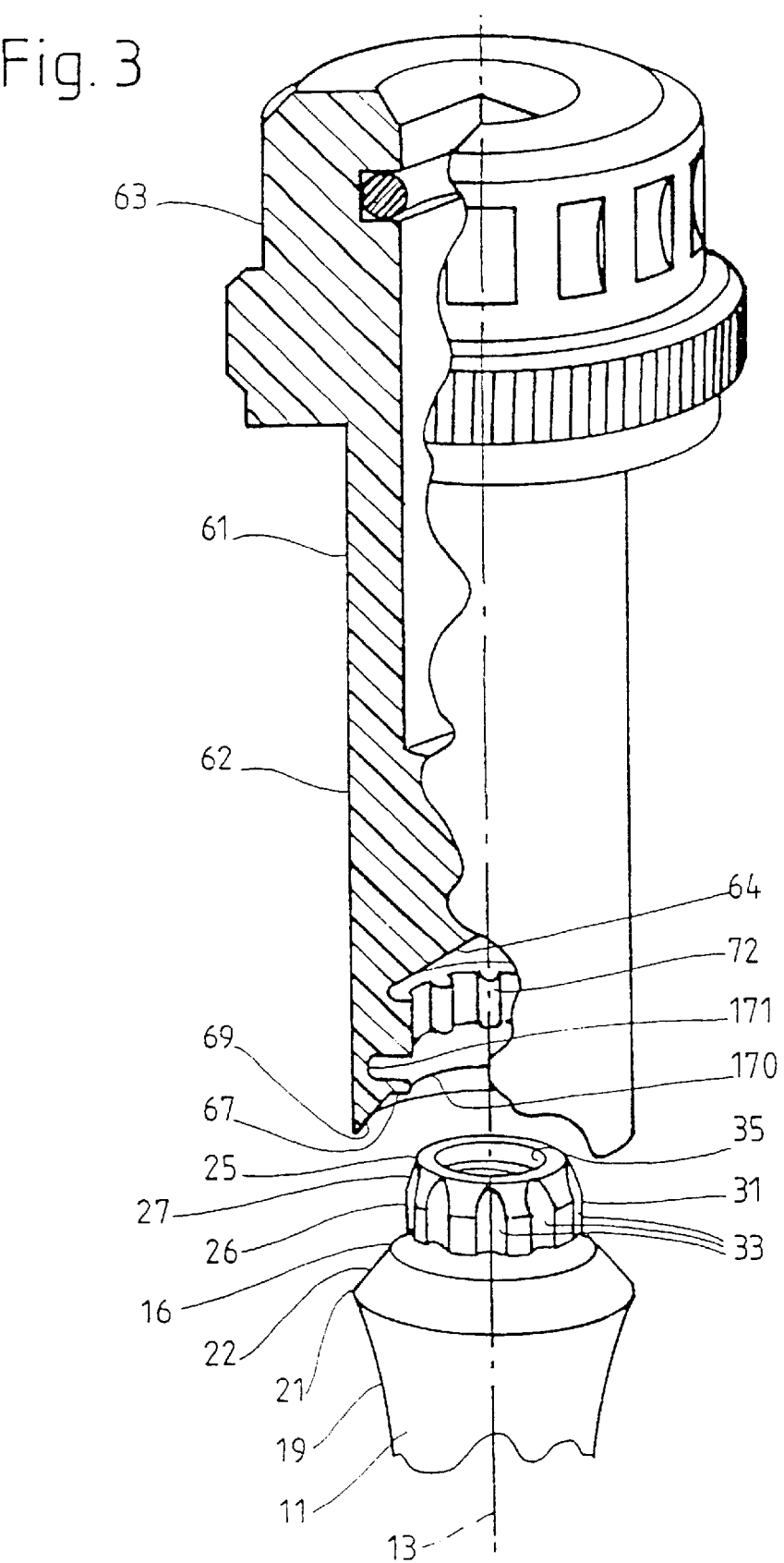
Figure 4:
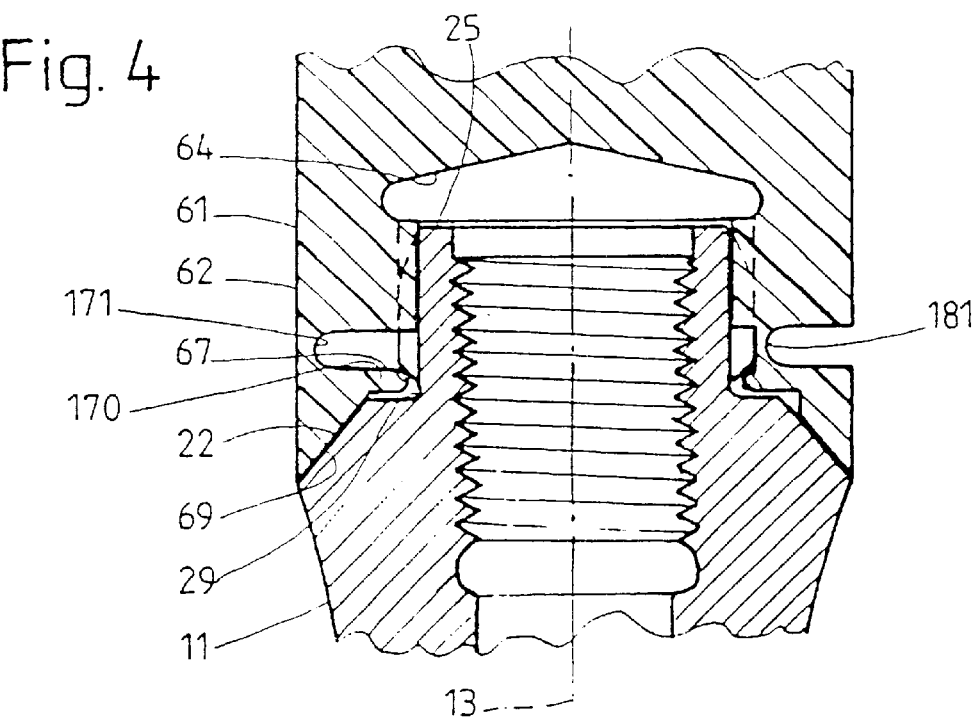

The dental implant 11 seen in FIGS. 3 and 4 is of the same configuration as the implant of FIGS. 1 and 2. The holder 61 seen in FIG. 3 and in the left half of FIG. 4 is also made similar to the holder 61 in FIGS. 1 and 2, but differs in that its shaft reaches only to the outer margin of the conical shoulder surface 22 and has catching and/or gripping means 67 which have an annular projection 170 disposed above the conical contact surface 69. This projection is separated by an annular groove 171 present in the blind bore 64 from the antirotational means 72 of the holder, and is connected in the bottom of this annular groove 171 by a relatively thin, resiliently deformable portion with the portion of the holder 62 situated above the projection 170. For connection to the implant 11, when the shaft 62 of the holder 61 is pushed approximately parallel to the axis 13 over its head, the head causes a momentary elastic deformation of the lower, free end section of the shaft. At the same time the annular projection 170 of the clutching or catch means is momentarily expanded slightly and then snaps, according to FIG. 4, into the annular groove 29 of the implant. By pulling the holder 61 axially from the implant 11, the projection 170 can be snapped back out again.

The holder 61 drawn on the right half of FIG. 4 is largely similar to the one on the left half, but differs in that, instead of the annular groove 171 created in the blind bore 64, it has an externally created annular groove 181.

Figure 5:
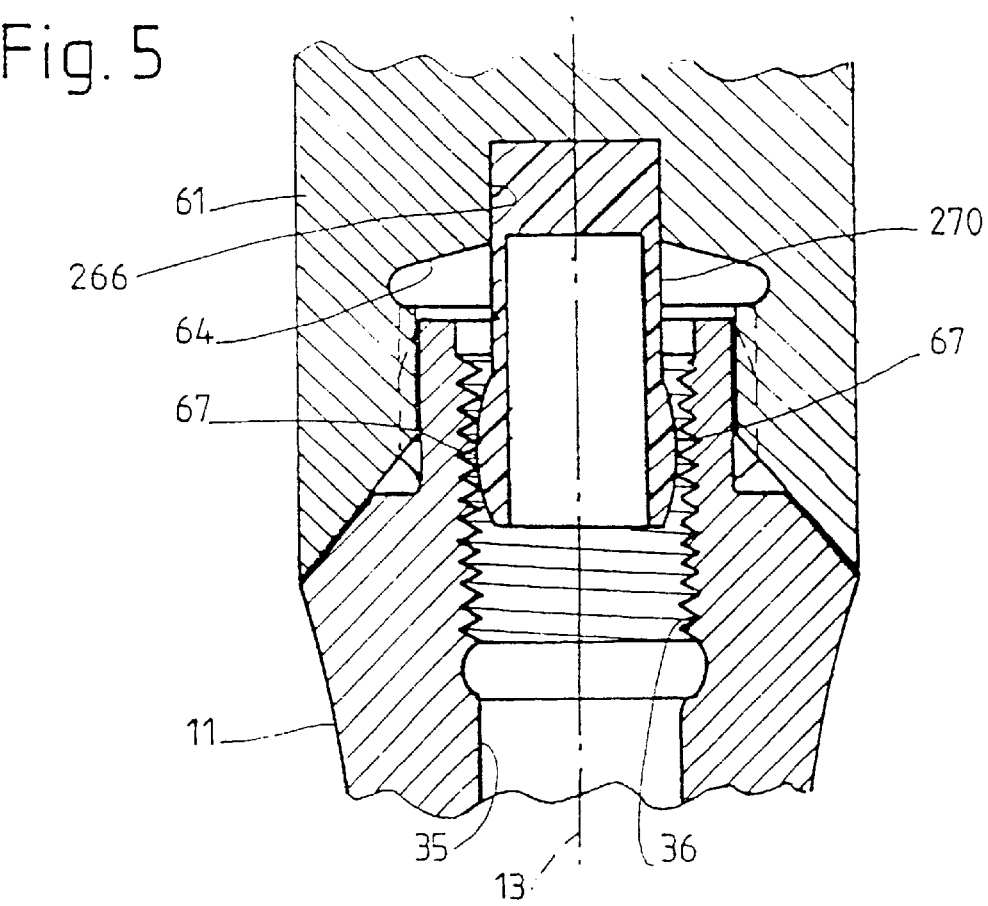

The blind bore 64 in the holder 61 drawn in FIG. 5 has at its inner end a cylindrical seat 266. The upper end of a generally cylindrical sleeve 270 is fastened therein. It is open at its bottom, free end. The end section thereof, at this end of the sleeve, is slightly thickened, has an exterior surface that is given a slightly convex curvature, is resiliently deformable in an approximately radial direction, and forms the clutching and/or catching means 67 of the holder 61 shown in FIG. 5. If it is joined to the implant 11, the sleeve penetrates into the blind bore 35 of the implant 11. The clutching and/or catching means 67 then enter the internal thread 36 of the blind bore 35 and removably clutch the implant.

Unless otherwise described above, the holders drawn in FIGS. 3 to 5 can be of the same or similar configuration as the holder described in FIGS. 1 and 2. Also, features of the various holders can be combined together.

Furthermore, the external thread 18 of the implant can be omitted and its anchoring portion can be configured such that it can be pushed into the bore in the bone parallel to the axis. The implant can then, when inserted into the hole in the bone, be positioned in a desired rotational position if necessary. The bore and the anchoring portion of the implant can then also be dimensioned and configured such that the implant must be hammered and/or pressed into the bore. To anchor the implant in the bone, a hammering and/or pressing tool can be struck or pressed against the head 63 of the holder 61. The holder 61 can then serve as a driving and/or pressing instrument. In any case, the procedure for removing the implant from the container and inserting it into a bone is similar to that for a screw implant, in which case the packaging according to the invention also offers similar advantages.

What is claimed is:

1. A package comprising a receptacle comprised of two receptacle parts and, disposed in the receptacle, a dental implant which has an anchoring portion intended for anchoring in a bone and an outer portion intended to protrude from the bone and an axis, the receptacle containing a holder having at least one of clamping and catching means for engaging said outer portion of the dental implant and releasably holding the dental implant, wherein the dental implant as well as the holder have anti-rotational means for mutual anti-rotational connection with respect to the axis, wherein the at least one of clamping and catching means as well as the anti-rotational means are configured such that the dental implant is removable together with the holder when the holder is removed from the receptacle and that the holder is separable from the dental implant by a shifting of the holder substantially parallel to the axis without removing any additional separate connecting means.

2. The package according to claim 1, wherein the holder has coupling means to connect the holder to a tool releasably and, with respect to the axis anti-rotationally.

3. The package according to claim 2, wherein the coupling means have a substantially cylindrical section with recesses distributed along a circumference of the cylindrical section.

4. The package according to claim 2, wherein the holder has an end facing away from the dental implant and an at least partially polygon-shaped bore opening into the holder and belonging to the coupling means.

5. The package according to claim 4, wherein the at least partially polygon-shaped bore of the holder has an annular groove which holds an elastic ring which projects at least in places out of the annular groove.

6. The package according to claim 1, wherein the holder has a shaft and a head projecting radially beyond the shaft, and the at least one of clamping and catching means is disposed at the end of the holder opposite from the head of the shaft, and wherein the head is provided with ridges or roughening.

7. The package according to claim 6; wherein the shaft, the at least one of clamping and catching means as well as the head consist of a one-piece body of plastic.

8. The package according to claim 6, wherein the receptacle encloses the dental implant and the holder completely and at least approximately tightly and contains an interior receptacle which is transparent, has an end with an opening and contains the dental implant and the shaft of the holder, and wherein the head of the holder is releasably fastened to the interior receptacle and closes the opening of the interior receptacle.

9. The package according to claim 1, wherein the anchoring portion of the implant has an external thread designed for screwing into a bore in the bone or is configured for axially parallel introduction into a bore in the bone.

10. The package according to claim 1, wherein the dental implant has at an end remote from the anchoring portion a head with anti-rotational surfaces non-rotationally symmetrical with the axis and pertaining to the anti-rotational means, and the dental implant has between the anchoring portion and the head a shoulder surface forming an angle with the axis, and wherein the holder has a contact surface lying on the shoulder surface and a bore guiding the head at least point-wise, and sections pertaining to the anti-rotational means of the holder and engaging anti-rotational surfaces of the head.

11. The package according to claim 10, wherein the anti-rotational means is formed by axial anti-rotational grooves.

12. The package according to claim 1, wherein the at least one of clamping and catching means comprises at least one elastically deformable portion.

13. A package comprising a receptacle comprised of two receptacle parts and, enclosed in the receptacle, a dental implant which has an anchoring portion intended for anchoring in a bone and an outer portion intended to protrude from the bone and an axis, the receptacle enclosing a holder having at least one of clamping and catching means to engage said outer portion of the dental implant, said at least one of clamping and catching means comprises at least one elastically deformable portion and is at least one of axially projection over an outer margin of a shoulder surface of the dental implant and releasably holding fast said outer margin, and of releasably catching an annular groove present on the outside of the dental implant, and of releasably engaging an internal thread of an axial bore of the dental implant which opens into a free end of said outer portion of the dental implant, so that the holder releasably holds the dental implant in such a way that the dental implant is removable together with the holder when the holder is removed from the receptacle and that the holder is separable from the dental implant by a shifting of the holder substantially parallel to the axis and wherein the dental implant as well as the holder have anti-rotational means for mutual anti-rotational connection with respect to the axis.

14. The package according to claim 13, wherein the holder has coupling means to connect the holder to at least one of a tool and of an instrument releasably, and with respect to the axis, anti-rotationally.

15. The package according to claim 14, wherein the coupling means have a generally cylindrical section with recesses distributed along a circumference of the cylindrical section and wherein the holder has an end facing away from the dental implant and an at least partially polygon-shaped bore opening into the holder and belonging to the coupling means.

16. The package according to claim 15, wherein at least partially polygon-shaped bore of the holder has an annular groove which holds an elastic ring and which projects at least in places out of the annular groove.

17. The package according to claim 16, wherein the at least one of clamping and catching means is at least one of axially projecting over an outer margin of the shoulder surface and holding fast said outer margin, of engaging an annular groove present in one of the head and the connection of the head to the shoulder, and of engaging an internal thread of an axial bore of the implant, which opens into a free end of the implant head.

18. A package comprising a receptacle comprised of two receptacle parts and, enclosed in the receptacle, a dental implant which has an anchoring portion intended for anchoring in a bone and an outer portion intended to protrude from the bone and an axis, the receptacle containing a holder having at least one of clamping and catching means to engage said outer portion of the dental implant and releasably hold the dental implant, wherein the dental implant as well as the holder have anti-rotational means for mutual anti-rotational connection with respect to the axis, wherein the at least one of clamping and catching means as well as the anti-rotational means are configured such that the dental implant is removable together with the holder when the holder is removed from the receptacle and that the holder is separable from the dental implant by a shifting of the holder substantially parallel to the axis, wherein the holder has an end facing away from the dental implant and coupling means to connect the holder to at least one of a tool and of an instrument releasably and, with respect to the axis anti-rotationally, wherein the coupling means have a generally cylindrical section with recesses distributed along a circumference of the cylindrical section and an at least partially polygon-shaped bore opening into the holder and belonging to the coupling means.

19. The package according to claim 18, wherein the at least partially polygon-shaped bore of the holder has an annular groove which holds an elastic ring projecting at least in places out of the annular groove.

20. The package according to claim 18, wherein the at least one of clamping and catch means is at least one of axially projecting over an outer margin of the shoulder surface and holding fast said outer margin, of engaging an annular groove present in one of the head and the connection of the head to the shoulder, and of engaging an internal thread of an axial bore of the implant, which opens into a free end of the implant head.

* * * * *